(12) United States Patent
Peuker et al.

(10) Patent No.: US 8,292,619 B2
(45) Date of Patent: Oct. 23, 2012

(54) DOSE DELIVERY SYSTEM

(75) Inventors: Marc Peuker, Schondorf (DE); Arno Hohmann, Munich (DE); Helmut Pauser, Diessen (DE)

(73) Assignee: 3M Deutschland GmbH, Neuss (DE)

( * ) Notice: Subject to any disclaimer, the term of this patent is extended or adjusted under 35 U.S.C. 154(b) by 477 days.

(21) Appl. No.: 10/598,343

(22) PCT Filed: Feb. 25, 2005

(86) PCT No.: PCT/EP2005/002017
§ 371 (c)(1),
(2), (4) Date: Aug. 24, 2006

(87) PCT Pub. No.: WO2005/084819
PCT Pub. Date: Sep. 15, 2005

(65) Prior Publication Data
US 2008/0227052 A1 Sep. 18, 2008

(30) Foreign Application Priority Data

| Feb. 27, 2004 | (EP) | .................................... 04004596 |
| Mar. 8, 2004 | (EP) | .................................... 04005468 |
| Mar. 9, 2004 | (EP) | .................................... 04005614 |

(51) Int. Cl.
*A61C 5/04* (2006.01)
(52) U.S. Cl. .......................................... 433/89
(58) Field of Classification Search ............ 433/80, 433/89, 90; 222/87, 88, 129, 135, 137, 145.1, 222/145.5, 145.6; 604/19, 82–92, 93.01, 604/181, 187, 218; 366/177.1, 176.1
See application file for complete search history.

(56) References Cited

U.S. PATENT DOCUMENTS

| 2,628,004 | A | * | 2/1953 | Schlicksupp | ................. 222/493 |
| 3,098,483 | A | | 7/1963 | Nielsen | ......................... 128/220 |
| 3,729,032 | A | * | 4/1973 | Tischlinger et al. | ............. 141/2 |
| 4,040,420 | A | * | 8/1977 | Speer | ................. 604/82 |
| 4,141,474 | A | * | 2/1979 | Nilson | ......................... 222/493 |
| 4,696,415 | A | * | 9/1987 | Meshberg | ....................... 222/82 |
| 4,738,660 | A | | 4/1988 | Lucas | ........................... 604/139 |
| 4,744,494 | A | | 5/1988 | Seager | |
| 4,813,433 | A | | 3/1989 | Downey | ...................... 128/765 |
| 4,978,336 | A | | 12/1990 | Capozzi et al. | ................. 604/82 |
| 5,737,437 | A | * | 4/1998 | Nakao et al. | .................. 382/101 |
| 6,007,515 | A | * | 12/1999 | Epstein et al. | ................. 604/82 |
| 6,264,619 | B1 | * | 7/2001 | Ferguson | ..................... 600/573 |
| 6,290,682 | B1 | | 9/2001 | Myers | ......................... 604/247 |
| 6,328,229 | B1 | | 12/2001 | Duronio et al. | ............. 239/399 |
| 6,544,233 | B1 | * | 4/2003 | Fukui et al. | .................. 604/191 |
| 6,547,101 | B1 | * | 4/2003 | Sogaro | ......................... 222/137 |
| 6,616,012 | B2 | * | 9/2003 | Dark | ................................ 222/1 |
| 2003/0186190 | A1 | * | 10/2003 | Lokhandwala et al. | ........ 433/89 |
| 2004/0024353 | A1 | * | 2/2004 | Petersen et al. | ................. 604/82 |

(Continued)

FOREIGN PATENT DOCUMENTS
DE 25 14 201 10/1976
(Continued)

*Primary Examiner* — Cris L Rodriguez
*Assistant Examiner* — Eric Rosen
(74) *Attorney, Agent, or Firm* — Peter L. Olson; Dean M. Harts (57) ABSTRACT

The present invention is directed to a unit dose delivery system for flowable substances. The delivery system or applicator of the present invention allows storage, mixing and well controlled dispensing of multi-material component substances.

7 Claims, 12 Drawing Sheets

U.S. PATENT DOCUMENTS

2004/0072123 A1*  4/2004  Simonton et al. ............... 433/80
2007/0060894 A1*  3/2007  Dai et al. ...................... 604/207

FOREIGN PATENT DOCUMENTS

| | | |
|---|---|---|
| DE | 201 07 507 U1 | 3/2002 |
| DE | 102 33 925 A1 | 2/2004 |
| EP | 0 689 874 A1 | 1/1996 |
| EP | 1 188 455 A1 | 3/2002 |
| WO | WO 91/03224 | 3/1991 |
| WO | WO 94/22507 | 10/1994 |
| WO | WO 97/14460 | 4/1997 |
| WO | WO 2004/017988 A1 | 3/2004 |

* cited by examiner

DOSE DELIVERY SYSTEM

CROSS REFERENCE TO RELATED APPLICATIONS

This application claims priority from European Application No. 04004596.5, filed Feb. 27, 2004; European Application No. 04005468.6, filed on Mar. 8, 2004 and European Application No. 04005614.5, filed on Mar. 9, 2004, the disclosure of which are incorporated by reference in their entirety herein.

The present invention is directed to a unit dose delivery system for flowable substances. The delivery system or applicator of the present invention allows storage, mixing and well-controlled dispensing of multi-material component substances.

As dose delivery systems, standard syringe configurations are generally used. One of the drawbacks of standard syringe configurations is that syringe configurations having finger plates for material dispensing require a change of hand position when switching between dispensing and treatment. This can pose an inconvenience to the dentist. There are also syringe tips on the market for treating teeth which can be adapted to standard syringes (e. g. using Luer-lock coupling). However, those tips are generally used only to spread substances on a surface and may not be adequate for providing sufficient mechanical force to the surface.

Further, some delivery systems do not have a means for storing and mixing material components and, therefore, may be inconvenient when delivering substances which are made of material components that have to be mixed just before use. In this case, the material components have to first be mixed and then filled into the system. This represents a disadvantage in terms of length of preparation and clean-up.

Further, some delivery systems, which enable storage and mixing of multi-material component substances, do not have adequate sealing means for the material components.

Therefore, there is a need for an improved dose delivery system and method offering improved handling, minimal effort for preparation and flexibility in terms of providing both controlled delivery and application of the substance.

The object of the present invention is to provide improved systems and respective methods. This object is achieved with the features of the claims.

The present invention is advantageous in that the delivery system is designed to allow dispensing and possibly treating using a single hand and without changing hand position. The present invention can be designed to be held like a pen or a dental instrument.

The present invention is advantageous in that the delivery system provides precisely-controlled dispensing of a substance.

The present invention is advantageous in that material components for substances can be pre-filled and stored in the delivery system and then mixed automatically within the system prior to or during use. Therefore, there is no effort for preparation. Also, since the delivery system of the present invention is disposable, there is no effort for cleaning the system after use.

The present invention is flexible in that a delivery system is provided which can also be used for cases where mixing and dispensing have to be separate procedures, i.e. two-step procedures.

The present invention also provides advantageous designs for tightly sealing the material components using foil only, thereby eliminating the need for using additional parts, such as plug sealants.

Further advantages will be apparent from the following description and drawings of the preferred embodiments of the present invention.

Figure 1:
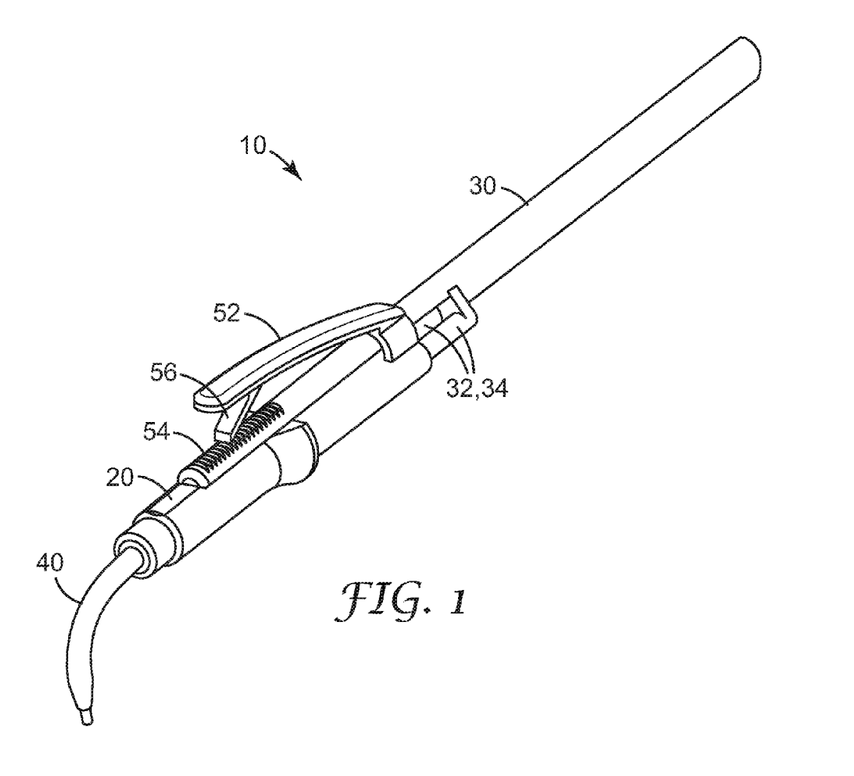
FIG. 1 is a perspective view of an embodiment of the delivery system of the present invention.
Figure 2:
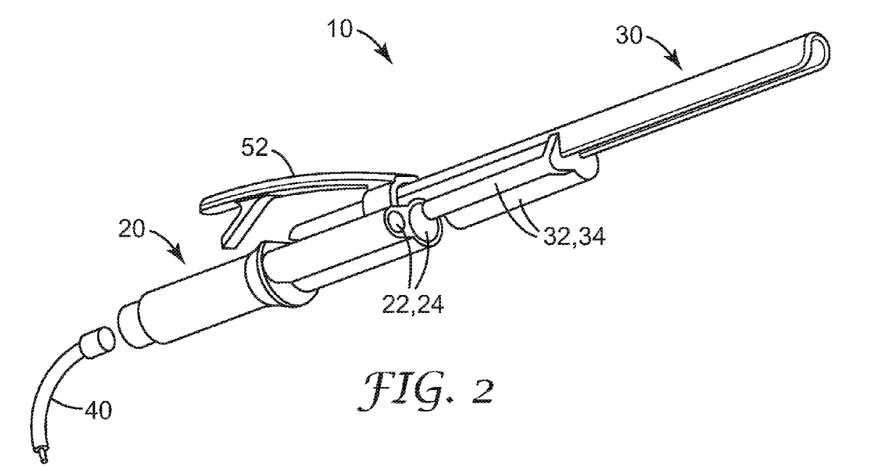
FIG. 2 is another perspective view (from below) of the embodiment shown in FIG. 1.

In one preferred embodiment of the present invention as shown in FIGS. 1 and 2, the delivery system 10 generally comprises a cartridge 20 having two compartments 22, 24 for storing material components and mixing means for mixing the material components, a plunger 30 having pistons 32, 34 associated with and corresponding to material compartments 22, 24, and actuating means for enabling controlled dispensing of the mixed material substance.

The cartridge 20 of the delivery system 10 has a body which is preferably made of relatively stiff material, for example polyoxymethylene. As shown in a cross-sectional view of the cartridge 20 in FIG. 3, the cartridge 20 comprises a mixing means and material compartments 22, 24. The compartments or chambers 22, 24 provide means for storing material components or substances in separate areas within the delivery system. This allows the system to pre-fill and store material components until use. Although only two material compartments are shown in the various described embodiments, it would be possible to have more than two material compartments containing different material components, if desired. Each material compartment 22, 24 is in fluid communication at one end with the mixing means of the cartridge 20 such that when actuated the material components are transferred into the mixing means.

The cartridge 420 of the present invention may also be formed by several separable components. For example, the cartridge 420 may comprise an actuator part 420a integrating part 452 of the actuation means 452, 454 and a material receptacle 420b having material compartments for containing material components. In this embodiment, the material receptacle 420b is exchangeable and thus separable from the actuator part 420a of the delivery system. This provides several advantages, e.g. in terms of costs. For one, the user merely has to replace the material receptacle when new or different substances have to be dispensed. Another advantage is provided by the possibility to use different polymers for the actuator part (e.g. POM, polyoxymethylene) and the material receptacle (e.g. polypropylene). The polymer for the actuator part may be chosen for achieving good mechanical performance while the polymer for the material receptacle may be chosen for optimum compliance to the material components.

Figure 3:
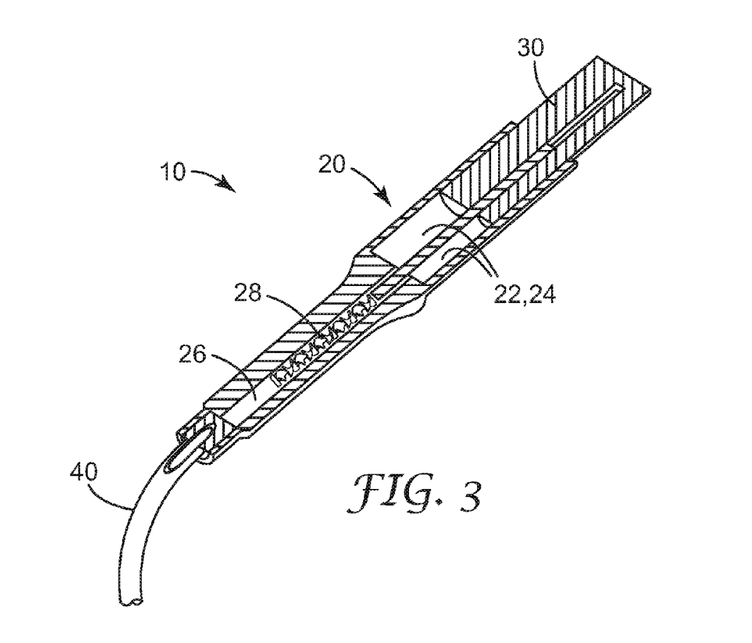
FIG. 3 is a cross-sectional view of an embodiment of the delivery system of the present invention.

The mixing means comprises a mixing barrel 26 and a mixer for mixing the material components. Preferably, the mixer comprises a static mixer 28 for passively mixing the components, wherein the material components are mixed as these components flow within the mixing barrel 26 and through the static mixer 28.

Figure 4A:
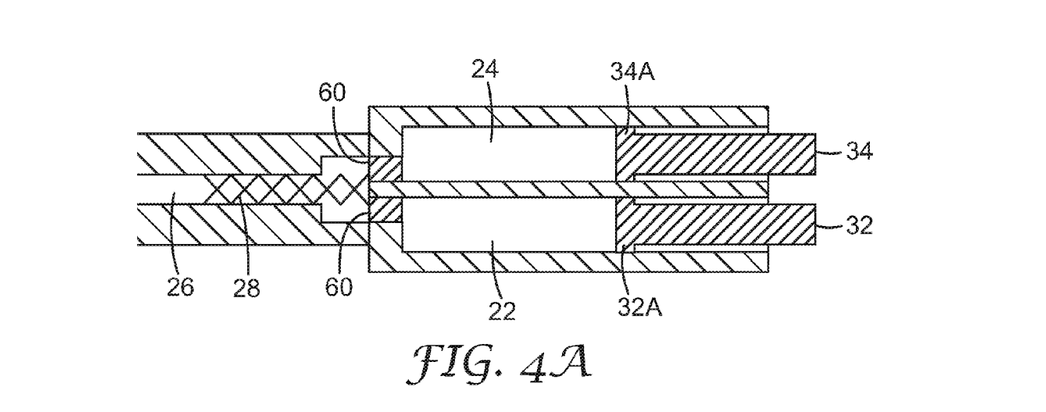
FIGS. 4A is a cross-sectional view of an embodiment of a sealing means for the present invention in a closed position.
Figure 4B:
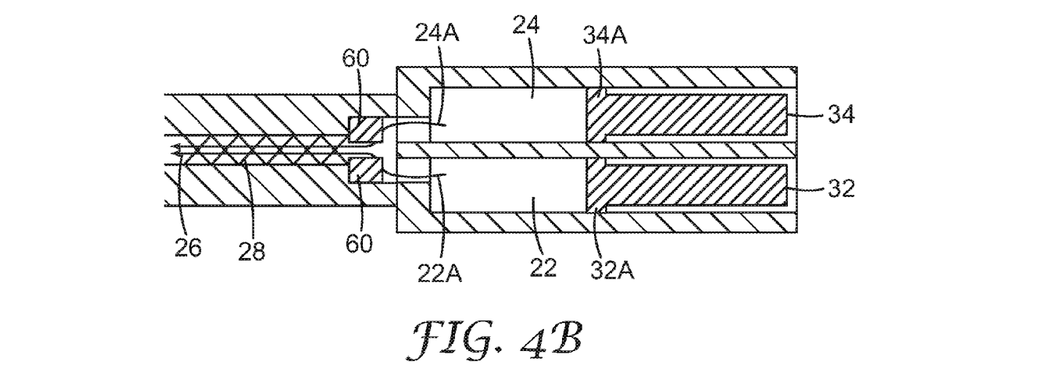
FIGS. 4B is a cross-sectional view of an embodiment of a sealing means for the present invention in an open position.

Once activated, the plunger of the delivery system of the present invention primarily serves to apply pressure to the material components contained within the compartments of the cartridge, thereby causing the material components to flow into the mixing means of the cartridge where the components are mixed. While deactivated, the plunger of the delivery system may serve as a sealing means for the back ends of the compartments. The plunger 30 of the delivery system 10 is preferably made of relative soft elastic material, for example high density polyethylene. As shown particularly in the embodiments of FIGS. 1-5, the plunger has two sliding members in the form of pistons 32, 34 and possibly a surface 36 connecting the pistons 32, 34 at one end. Alternatively, the connecting surface 36 can be replaced with any means enabling the pistons to move uniformly. The pistons 32, 34 are designed to fit tightly and slideably into corresponding material compartments 22, 24. As seen in FIGS. 4A and 4B, each piston 32, 34 has a bulge 32a, 34a at its front end side forming a press fit with the material compartment 22, 24 thus providing a tight seal at the back end of the compartment. The other end or front end of the material compartment 22, 24 is in fluid communication with the mixing barrel 26 and sealed by a sealing means until the plunger 30 is actuated.

In order to prevent the material components from entering the mixing means before use, the delivery system of the present invention preferably comprises a sealing means. The sealing means should provide tight sealing of the compartments such that the material components are prevented from entering the mixing means before the plunger is actuated and should also allow flow of the material components into the mixing barrel once the plunger is actuated. One embodiment of the sealing means is shown in FIGS. 4A and 4B. In this embodiment, the sealing means comprises plugs 60 which are adapted to fit within outlets 22a, 24a at the front ends of the material compartments 22, 24. The plugs 60 serve to seal the outlet bores of the compartments, thereby preventing the material components from flowing into the mixing barrel 26 of the mixing means. The plugs 60 are preferably made of relative soft elastic material, for example high density polyethylene. The plugs 60 can be integrally molded together with the mixer 28 of the mixing means. Upon movement of the plunger 30 toward the front end the cartridge, the plugs 60 are pushed forward in the same direction as the plunger is moved thereby opening the outlets 22a, 24a and enabling the material components in the compartments 22, 24 to flow into the mixing barrel 26.

Conventional sealing means may also be used for the delivery system of the present invention.

An embodiment of the actuation means of the present invention is illustrated in FIG. 1. Here, the actuation means comprises a lever 52 integrally formed with the cartridge 20 and a geared connection rod 54 integrally formed with the plunger 30. The lever 52 has a pawl 56 which engages with teeth or slots located on the connection rod 54. Upon each push of the lever 52, the pawl 56 is bent which causes the edge of the pawl 56 to move in the direction of the longitudinal axis of the system 10 thus forcing the connection rod 54 to move clockwise forward. As a result, the plunger 30 is moved forward thereby causing the material components to flow into the mixing means and afterwards to exit as a mixed substance through the outlet of the cartridge 20. So each time the lever 52 is pushed, a small predetermined amount of material substance is extruded out of the delivery system thereby providing controlled delivery of the substance.

When the cartridge 20 is made of a relative stiff elastic material (e.g., polyoxymethylene), the lever 52 and pawl 56 will reset to their original positions after each push which makes additional retaining springs unnecessary.

Preferably, the delivery system of the present invention comprises a dispensing tip or nozzle 40 provided at the outlet of the cartridge 20, as shown in FIGS. 1-3 and 5-6.

The delivery system of the present invention may be also used for treating the teeth, especially in cases where repeated or continuous delivery of substance to the area to be treated is required or desirable during treatment. This eliminates the need to use separate instruments for application and treatment. To this end, the present invention may also comprise a means for treating teeth. The means for treating teeth is preferably designed to apply considerable mechanical force to the surface to be treated.

Figure 6:
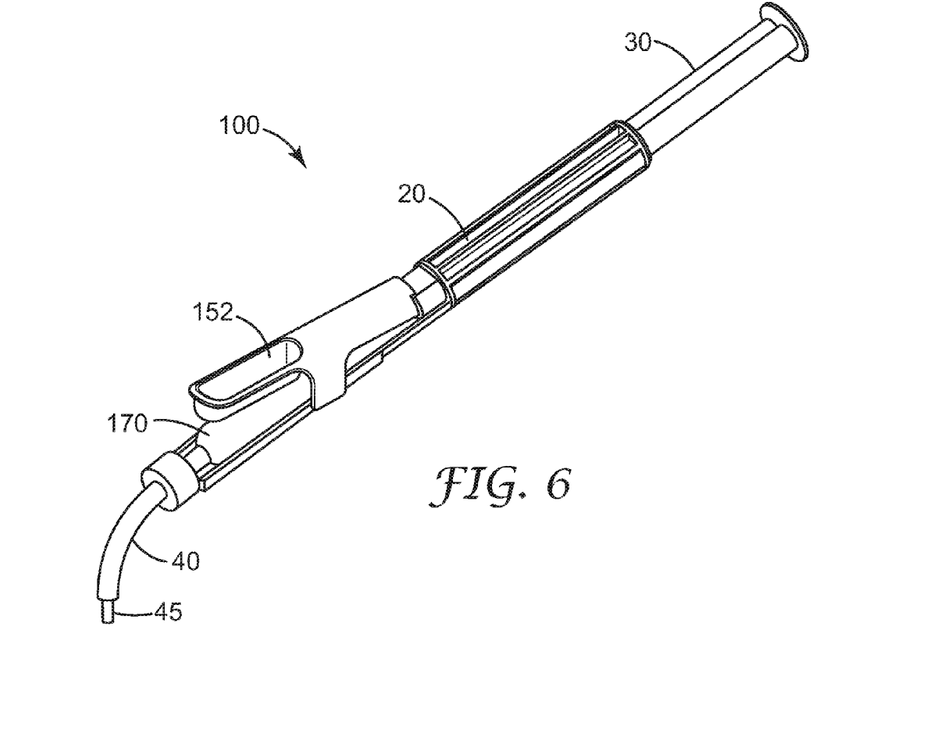
FIG. 6 is a perspective view of an embodiment of the present invention having an additional reservoir.

The means for treating teeth preferably comprises a brush. It has so far been proven advantageous to have the fibers or bristles of the brush 45 be arranged in the outlet bore of the nozzle 40 of the system, as shown in FIG. 6. Preferably, a bundle of straight fibers is formed by a press fit with the inner bore of the nozzle. The fibers are preferably made of PBT (polybutylene terephthalate) in order to achieve a relatively high stiffness for the brush. Other optional materials for the fibers comprise PA (polyamide), POM (polyoxymethylene), COC (cyclo olefine copolymer) and LCP (liquid crystal polymers). The diameter of the bundle is preferably 1.5 mm, and most preferably within the range of 1 to 2 mm. The diameter of the individual fibers is preferably 0.25 mm, and most preferably within the range of 0.1 to 0.5 mm. The length of the brush is preferably between 1 and 3 mm.

The brush 45 can be manufactured by any conventional means known in the art. For example, the brush 45 can be manufactured by integrally-molding the bristles and nozzle, by two shot injection molding the bristles and nozzle, or by flocking bristles on a ball-shaped tip.

In one aspect of the present invention, a delivery system is provided which enables a two-step procedure. Such a delivery system may be preferred when mixing and dispensing of the materials have to be separate procedures. In some cases it may be advantageous to mix the material components in a first step thereby activating the materials and forming a mixed substance and, then, to dispense the mixed substance in a second step. For example, when using a static mixer, the efficiency of the mixing depends on the flow rates of the material components flowing through the mixer. In order to achieve a more homogeneous mixing, a more or less rapid activation than achieved using a static mixer may be desirable.

Figure 5:
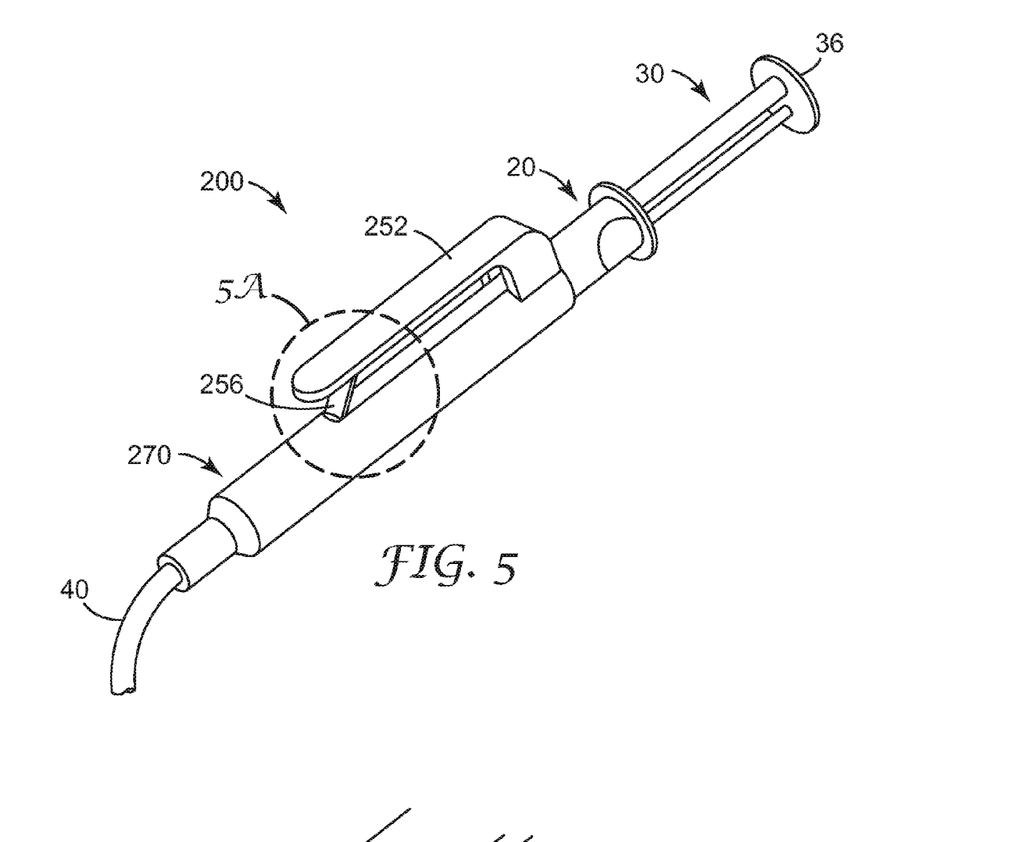
FIG. 5 is a perspective view of another embodiment of the delivery system of the present invention.
Figure 5A:
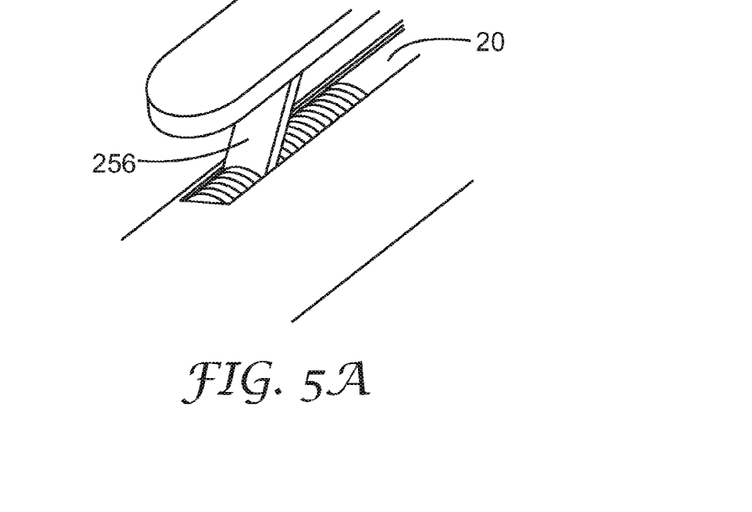
FIG. 5A is a perspective view of the actuation means of the embodiment shown in FIG. 5.
Figure 7:
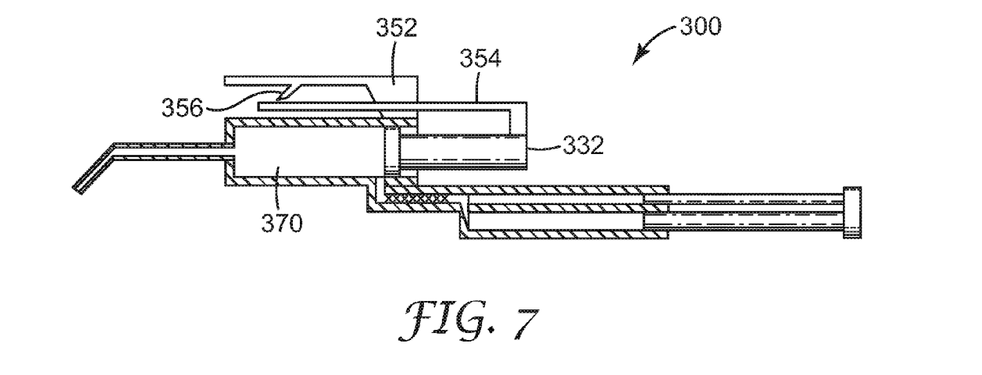
FIG. 7 is a schematic diagram of an embodiment of the present invention having an additional reservoir.

This aspect of the present invention is particularly described in FIGS. 5, 6 and 7. Each embodiment of this aspect of the present invention comprises an additional reservoir 170, 270, 370 for receiving the mixed substance after it exits the mixing means of the cartridge 20. The mixed substance is then dispensed from this reservoir 170, 270, 370.

Further, in each of the embodiments of this aspect of the present invention, movement of the material components from the compartments into the mixing means is achieved by pushing the plunger 30 forward in the direction of the front end of the cartridge 20. This causes the material components to flow through the mixing means and to be activated as they mix.

Further, in each of the embodiments of this aspect of the present invention, the actuation means for mixing the material components is separate from the actuation means for dispensing the mixed substance and, therefore can be operated independently from each other. This enables the delivery system to be used in a two-step procedure wherein the material components are first mixed and stored in a reservoir and then dispensed from the reservoir in a later step.

In one embodiment of this aspect of the present invention as shown in FIG. 6, the delivery system 100 comprises a reservoir means for receiving and holding the mixed substance. The reservoir means is attachable to the outlet of the cartridge 20 of the delivery system 100. The reservoir means comprises a bladder 170, preferably in the form of a soft blister. The bladder 170 may be manufactured by any conventional method, for example, by blow molding. The bladder 170 is squeezed out by a lever 152 that is step by step pushed from an initial position to its end position. The lever is mechanically disabled from moving back into its initial position, thereby having a locking mechanism in one direction. Each time the bladder 170 is squeezed by the lever 152, a pre-determined amount of mixed substance is extruded from the bladder 170 thereby providing controlled delivery of the mixed substance.

In a second embodiment of this aspect of the present invention as shown in FIG. 5, the delivery system 200 also comprises a reservoir for receiving and holding the mixed substance. Preferably, the reservoir 270 is formed by the outer surface of the cartridge 20 and the inner surface of a movable sleeve, wherein a cavity is preferably formed therein. For dispensing the mixed substance, the cartridge 20 is moved into the sleeve thus forcing the mixed substance out through the nozzle 40 of the system 200. Movement of the cartridge is done by actuation means. Here, the actuation means preferably comprises a lever 252 integrally formed with the movable sleeve 270. Slots are preferably formed on the cartridge 20. Preferably, the lever 252 has a pawl 256 which engages with the slots of the cartridge 20. Upon each push of the lever 252, the pawl 256 is preferably bent which causes the edge of the pawl 256 to move in the direction of the longitudinal axis of the system 200 thus forcing the cartridge 20 to move forward. Preferably, the lever 252 and pawl 256 are integrally made with the sleeve 270 using a one shot molding technique.

A third embodiment of this aspect of the present invention is shown in the schematic diagram of FIG. 7. In this embodiment, the delivery system 300 also comprises a reservoir for receiving the mixed substance after it exits the mixing means of the cartridge. As shown in FIG. 7, the delivery system 300 preferably comprises a dispensing means coupled to the outlet of a cartridge. The cartridge has preferably two compartments for storing material components and a mixing means for mixing the components. Preferably, the cartridge is activated by pressing the plunger forward into the mixing means. After exiting the mixing means, the mixed substance of material components may enter the dispensing means. Preferably, the dispensing means comprises actuation means and a reservoir 370 for receiving and holding the mixed substance. The actuation means preferably comprises a lever 352, a pawl 356, a connecting rod 354 and a plunger 332 having a piston. Preferably, the connecting rod 354 is attached to the rear end of the plunger 332 and has slots or teeth on its surface for engaging with the pawl 356. By pressing the lever 352, the pawl 356 engages with the connecting rod 354 thereby activating the plunger 332, and the piston of the plunger 332 is caused to move forward into the reservoir 370 thereby pushing the mixed substance forward into the nozzle 340 where the substance can be dispensed. Preferably, the dispensing means is adapted to provide precise dispensing of the substance. One of the advantages of this embodiment is that the delivery system does not shorten in length while dispensing.

Figure 14:
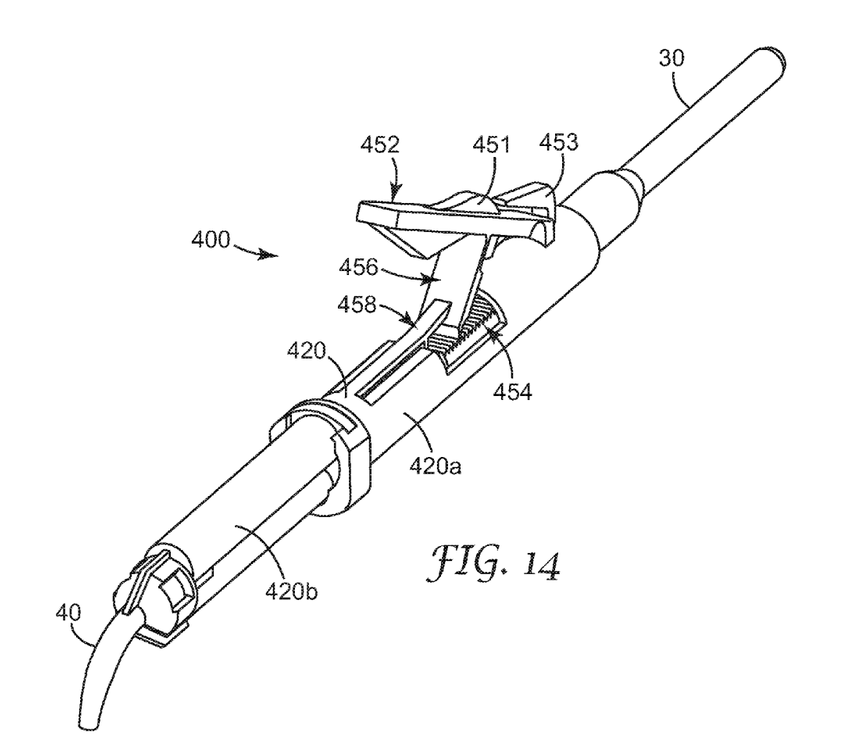
FIG. 14 is a perspective view of another embodiment of the delivery system of the present invention.
Figure 15:
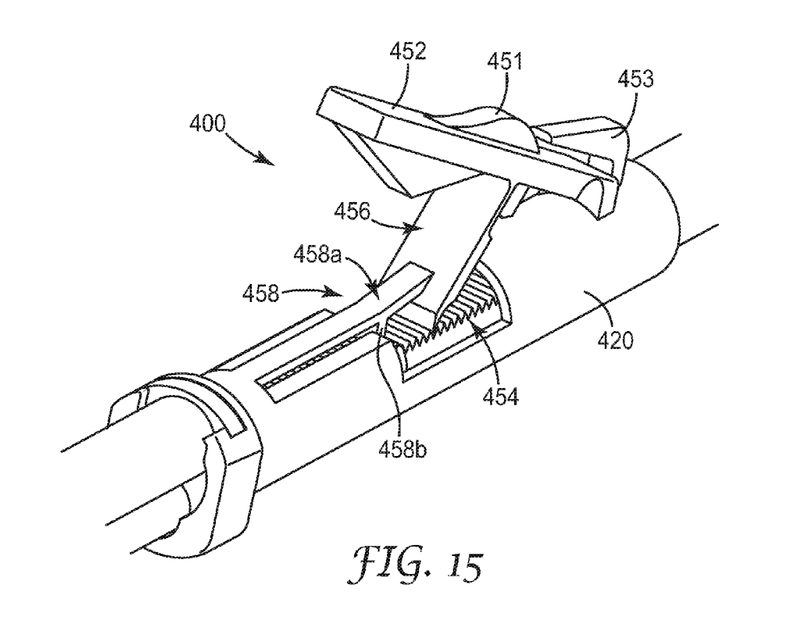
FIG. 15 is a perspective view of the actuation means of the embodiment shown in FIG. 14.
Figure 16:
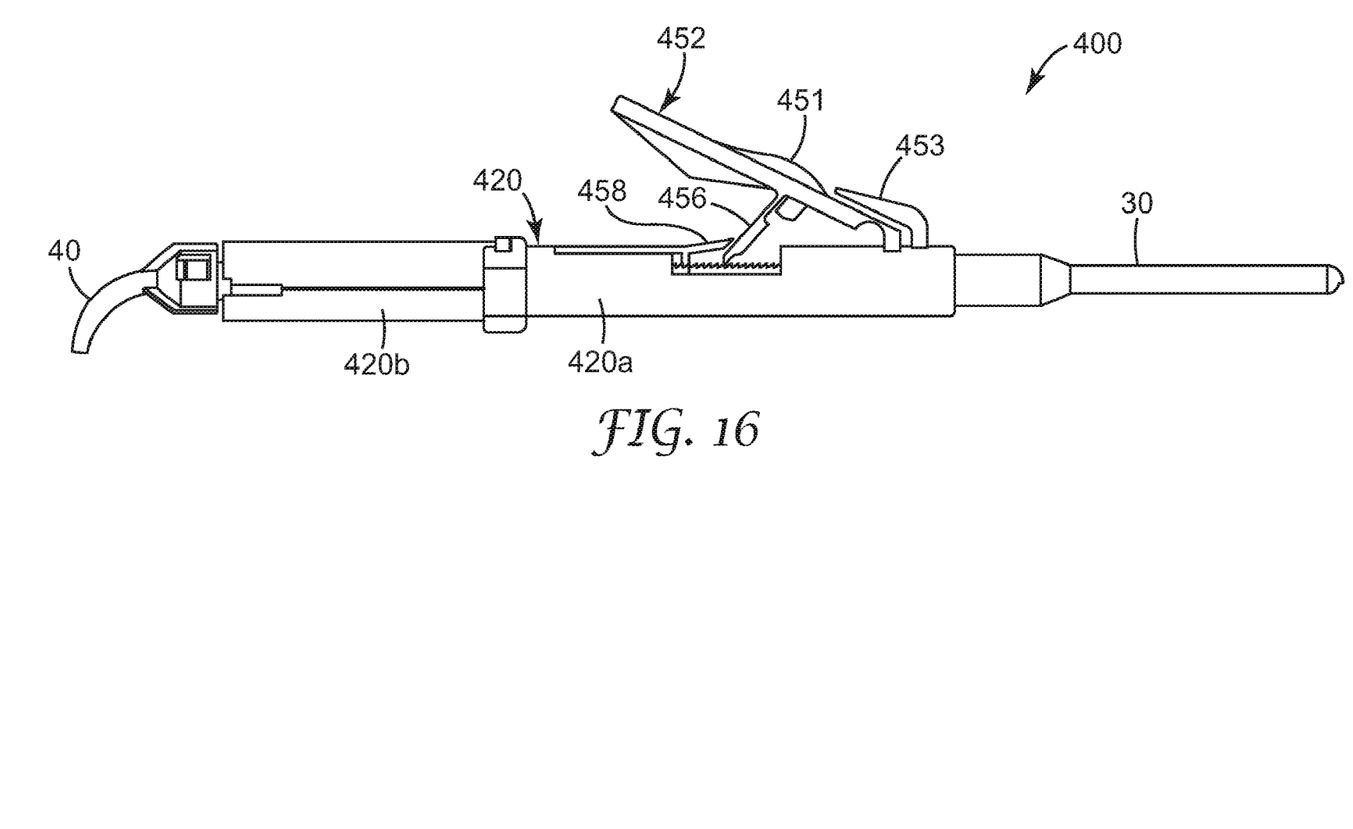
FIG. 16 is a side view of the embodiment shown in FIG. 14.

Another embodiment of the delivery system of the present invention is shown in FIGS. 14-16. The delivery system 400 comprises a cartridge 420 having compartments for storing material components, a plunger 30 having pistons associated with and corresponding to the material compartments and actuation means for enabling controlled dispensing of the mixed material substance. Also, the delivery system may have a dispensing tip 40 comprising a brush or other suitable means for treating the teeth.

The actuation means comprises a lever 452 integrally formed with the actuator part 420a of cartridge 420 and a geared connection rod 454 integrally formed with the plunger 30. The lever 452 has a pawl 456 which engages with teeth or slots located on the connection rod 454. In this embodiment, a reinforcement member 458 provides reinforcement for pawl 456 thereby enabling improved engagement of the pawl 456 into the slots of the connection rod 454 and hindering possible backlash movement of the connection rod 454. The reinforcement member 458 may be integrally formed with the actuator part 420a. As shown in FIG. 15, the reinforcement member 458 comprises an element 458a protruding horizontally in the direction of pawl 456 and having an edge which can contact the surface of the pawl 456. Preferably, the edge of the element 458a of the reinforcement member 458 and the surface of the pawl 456 are so designed that when the element 458a and pawl 456 contact, a downward force is exerted onto the pawl 456 thereby assisting the pawl's engagement into one of the slots of the connection rod 454. Preferably, element 458a of reinforcement member 458 is sufficiently deformable to reinforce engagement of the pawl 456 with the connection rod 454. The reinforcement member 458 may also comprise an element 458b which may engage with the slots of connection rod 454, thereby hindering possible backlash movement of the rod 454. The pawl 456 may also have a profile which provides improved engagement of the pawl tip into the slots of the connection rod 454, as can be seen particularly in FIG. 16.

Further, the actuation means of this embodiment may have a blocking member 453 which restricts the upward movement of lever 452. When the lever 452 is upwardly moved, the pawl 456 lifts reinforcement member 458 thereby releasing the connection rod 454 and enabling replacement of the receptacle 420b. A protrusion 451 may also be provided on the surface of lever 452 in order to allow an improved grip for the user.

Dispensing using the actuation means of this embodiment is similar to that of the previous embodiments. Upon each push of the lever 452, the pawl 456 is bent which causes the edge of the pawl 456 to move in the direction of the longitudinal axis of the system 400 and to engage with a slot of the connection rod 454 thereby forcing the connection rod 454 to move forward toward the dispensing tip 40 of the system. As a result, the plunger 30 is moved forward thereby causing the material components to flow into the mixing means and afterwards to exit as a mixed substance through the outlet of the dispensing tip. So each time the lever 452 is pushed, a small predetermined amount of material substance is extruded out of the delivery system thereby providing controlled delivery of the substance.

The mixing means can be a static mixer 28, e.g. as illustrated in FIG. 3, or just an orifice or outlet into which the material components are forced to flow together.

The cartridge 420 in this embodiment of the present invention may also be a cartridge formed of several separable parts. As previously described, the cartridge 420 may comprise an actuator part 420a and a material receptacle 420b, wherein the material receptacle 420b is separable from the actuator part 420a of the delivery system 400. The material receptacle 420b may have material compartments containing the material substances to be mixed and dispensed.

In another aspect of the present invention, the delivery system 10, 100, 200, 300, 400 comprises sealing means and a self-opening closure system as illustrated in FIGS. 8-13. The self-opening closure system can be used, for example, as an alternative to the sealing means described in FIGS. 4A and 4B.

Figure 8:
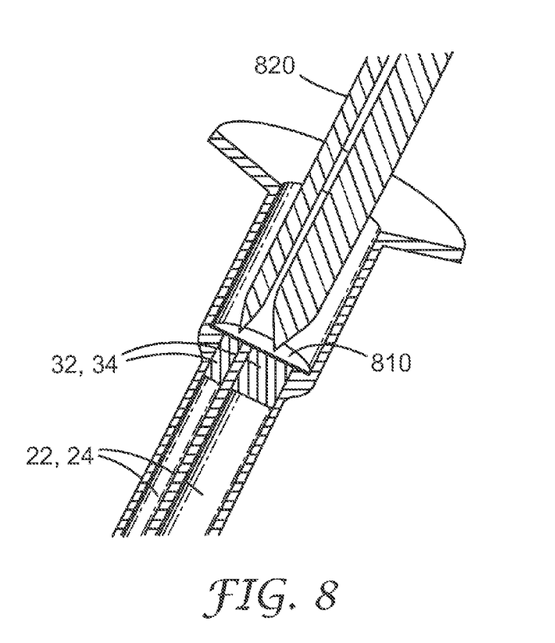
FIG. 8 is a perspective view of an embodiment of the present invention illustrating sealing means.

FIG. 8 shows a sealing means of the present invention using a sealing Material 810 to seal the material compartments of the cartridge. The sealing material is preferably foil. In this case, the pistons are preferably used only to push the material components. In one embodiment of the sealing means, the pistons are sealed in the compartments together with the material components. The plunger further comprises two pin rods 820 that are preferably shaped like sharp pins. The pin rods are used to penetrate the foil easily and then to push the pistons forward. In another embodiment, pistons are not used. Rather, the pin rods of the plunger are used to penetrate and push the foil forward thereby also pushing the material components forward. It has been found that, although the foil is penetrated by the pin rods, both of these embodiments properly sealed the material components as they are moved forward. In other words, there was no lost of material components, for example, due to the material seeping out around the pistons or pin rods.

Figure 9:
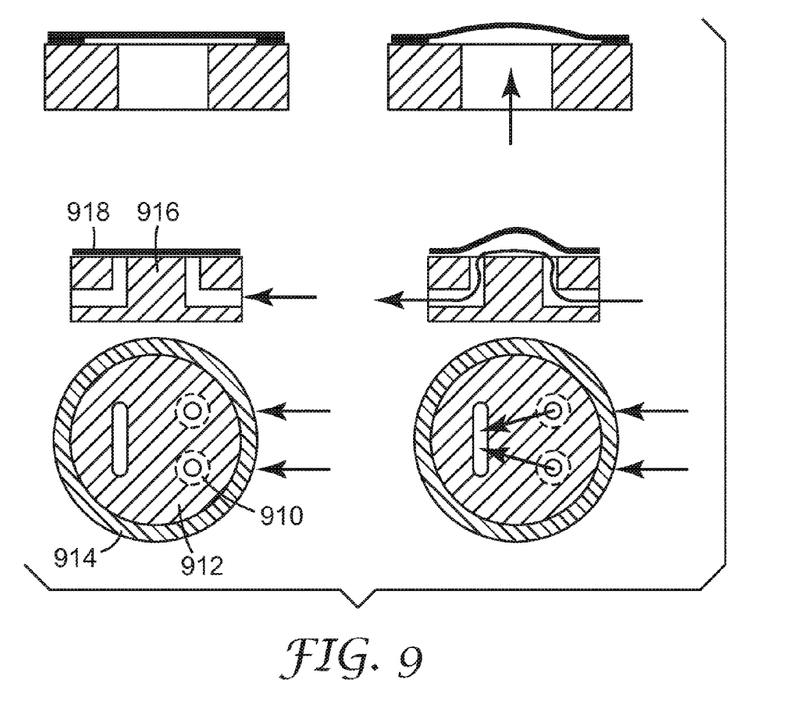
FIG. 9 is an illustration of material component flow in an embodiment of the self-opening closure system of the delivery system of the present invention.

The present invention also comprises a self-opening closure system at the front ends of the compartments. The closure system is self-opening in the sense that the closure system seals the front ends of the compartments until the plunger is activated thereby restricting the material components from flowing into the mixing means and opens when sufficient pressure is exerted by the material components which are pushed forward by the plunger when activated. The closure system preferably comprises at least one sealing material, at least two outlet bores connected to the material compartments and at least one inlet. The sealing material is permanently sealed along the circumference of an area at the front end of the cartridge. As shown in FIG. 9, the permanently sealed area 914 surrounds a non-permanently sealed area 912. The sealing material 918 can be permanently sealed along a ring 914 whereby the non-permanently sealed area 912 is within the ring. The area is "non-permanently sealed" in that this area is tightly sealed until sufficient pressure is applied by the material components being pushed by the plunger. Once sufficient pressure is exerted against the sealing material 918, the non-permanently sealed area 912 opens to allow the materials to flow, as illustrated in FIG. 9. The outlet bores 910 connected to the material compartments of the cartridge as well as the inlet connected to the mixing means are located within this non-permanently sealed area 912. During activation the fluid pressure forces the sealing material 918 to peel away from the base of the area 912. The sealing material 918 and the base form a chamber over the outlet bores 910 and the inlet thereby enabling the material components to flow over from the compartments into the mixing means.

Figure 10:
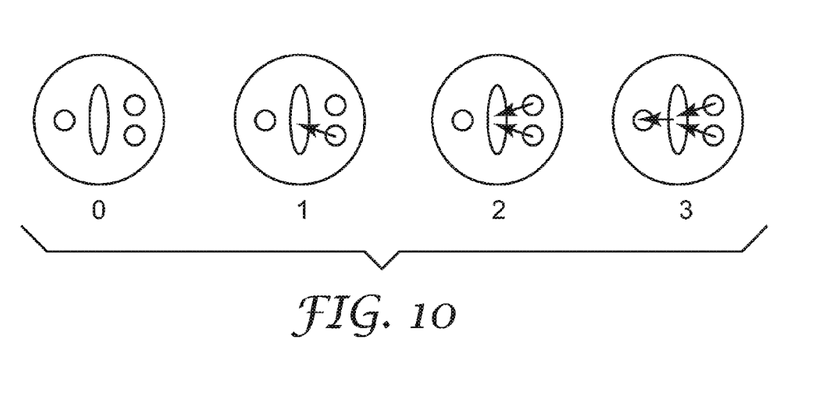
FIG. 10 is an illustration of material component flow in another embodiment of the self-opening closure system of the delivery system of the present invention.

In order to optimize the mixing of the material components, another embodiment of the self-opening closure system preferably comprises two seals. In this embodiment, a separate seal is preferably used for each compartment and two inlets are preferably used, instead of one inlet. Further, an intermediate chamber is preferably located between the inlet to the mixing means and the outlet bores of the compartments. This can be used to facilitate simultaneous opening of the two outlet bores, as shown in FIG. 10. In this case, if one bore opens earlier, the material will not flow into the inlet of the mixing means but into the inlet of the intermediate chamber. Since the plunger can only be further moved as soon as the bore of the second compartment also has been opened, activation of the intermediate chamber will only occur when both bores have been opened. When the intermediate chamber is activated, the material will continue to flow into the inlet of the mixing means. As an additional effect, the material component of the first bore located in the intermediate chamber may be utilized to backwardly activate the second bore.

The afore-described many aspects of the present invention may be combined in any manner to form various embodiments of the present invention.

Figure 11:
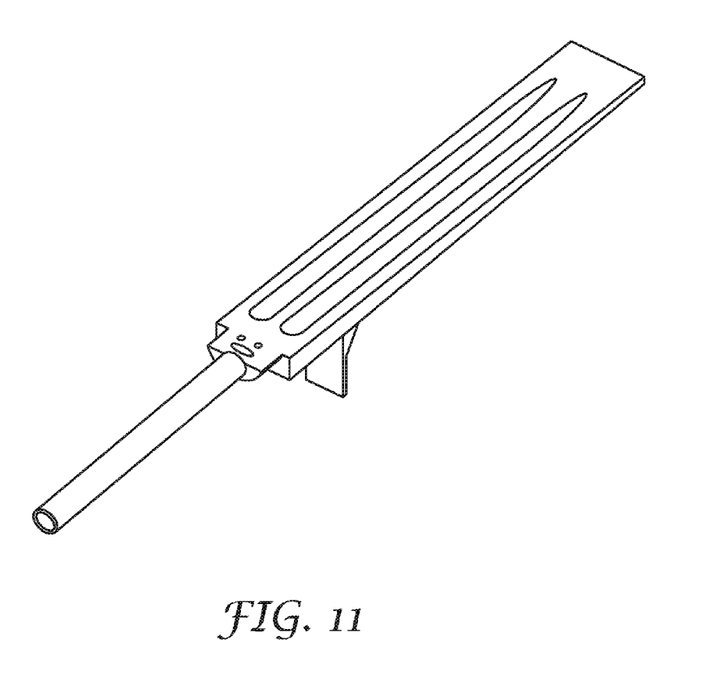
FIG. 11 is a cross-sectional view of an embodiment of the present invention with an embodiment of the self-opening closure system.
Figure 12:
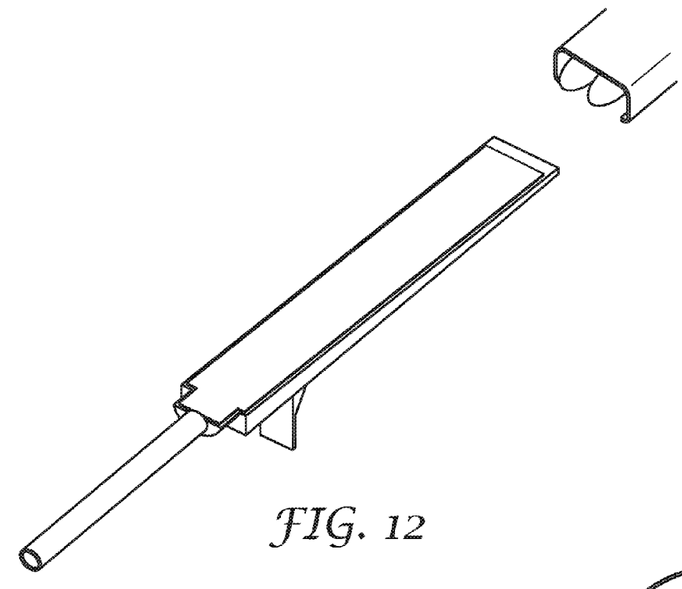
FIG. 12 is a perspective view of an embodiment of the present invention with sealing means.
Figure 13:
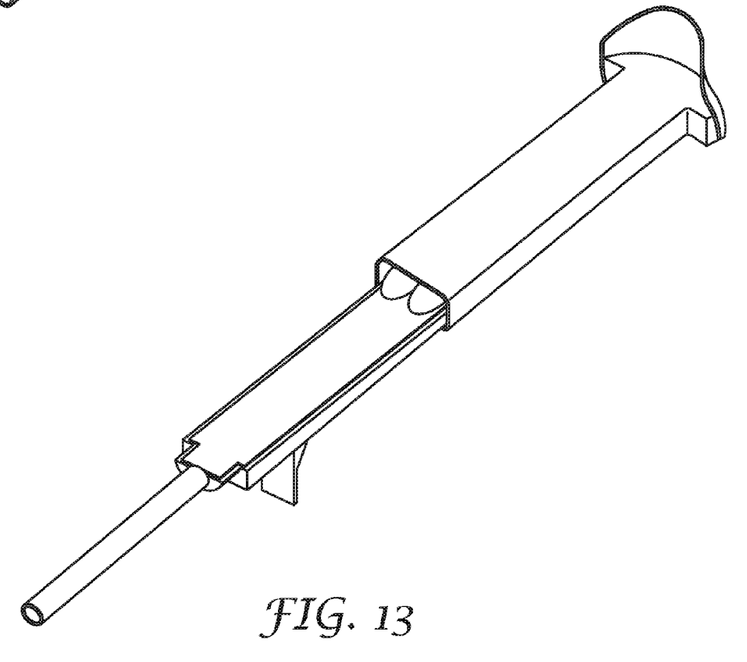
FIG. 13 is a perspective view of an embodiment of the present invention with sealing means.

For example, one preferred embodiment of the invention is described in FIGS. 11-13. In this embodiment, the delivery system comprises an embodiment of the self-opening closure system combined with the embodiment described in FIG. 6 having an additional reservoir in the form of a bladder. However, the sealing features of this embodiment can also be used in combination with any of the embodiments of FIGS. 1-3, 5, 7 and 14-16.

In this embodiment of the present invention as shown in FIG. 11, the cartridge has preferably grooved-shaped material compartments. The grooved-shaped compartments preferably taper from the front to the back end of the cartridge in order to provide optimal emptying of the compartments. Also, as seen in FIG. 11, the cartridge preferably further incorporates the base of a self-opening closure system as described above.

The grooved-shaped compartments filled with the material components are preferably covered and sealed by a sealing material, as shown in FIGS. 12 and 13. A sealing material preferably extends from the back end to the front end of the cartridge and preferably covers both material compartments and the closure system. As seen in FIGS. 12 and 13, the plunger has preferably two pistons or bulges for sliding into the grooves and pressing the sealing material covering the compartments. Preferably, the pistons are cylinder in shape and correspond to the shape of the grooved compartments. As the plunger is pushed forward, the bulges press the sealing material into the grooves thereby displacing and moving the material forward toward the self-opening closure system. Preferably, an actuation means as used in the embodiment of claim 6 is used also for precise dispensing of the mixed substance in this embodiment.

A system according to the present invention further preferably comprises at least one of the following materials: enzyme-containing compositions such as those described in WO 2004/017988; dental primers; bondings; etching gel/liquids; varnishes; glue, such as cyanoacrylate; pharmaceuticals, such as liquids and/or gels; a substance for the treatment or prevention or identification of caries; a substance for the prevention or identification or removal of plaque; a substance for root canal treatment; a substance for the removal of carious or decayed or infected dentine or enamel and/or a substance for the removal of denaturated dentine.

A system according to the present invention can be further comprised in a kit further comprising at least one of the following members: dental instruments, such as excavators, in particular disposable dental instruments; brushes, particularly of different sizes and hardnesses; disposable cartridges so that the system can be used as a refillable system; gloves and/or at least any one of the above mentioned materials; and/or bonding and/or etching agent/gel.

Also features shown in the attached drawings either alone or in any combination with other features and not explicitly mentioned in the description do belong to the present invention.

The present invention is not limited to the specific illustrated embodiments. Moreover, the present invention is realized by the features of the claims and any obvious modifications thereof.

The invention claimed is:

1. A delivery system for controlled dispensing of a substance, the system comprising:
   a cartridge having at least two compartments for storing material components, each of the at least two compartments having an outlet at a front end, wherein the system is adapted to mix the components to form a substance;
   a plunger having at least two pistons for sealing the respective compartments and advancing material components in the at least two compartments;
   a mixer for receiving the material components from the at least two compartments and for mixing the material components;
   a sleeve which is movable over the exterior surface of the cartridge;
   a reservoir for receiving the mixed substance from the mixer, wherein the reservoir is formed by an interior surface of the sleeve and an exterior surface of the cartridge, wherein a cavity is formed within the reservoir;
   a lever and a geared connection rod for providing controlled dispensing of the substance; and
   a self-opening closure system which seals the front ends of the at least two compartments and opens when the plunger is advanced;
   wherein the lever is attached to the sleeve, and a pawl engages with the lever so that upon each push of the lever, the cartridge is caused to move forward toward the cavity thereby providing controlled dispensation of the substance.

2. The delivery system according to claim 1, comprising a blocking member which restricts upward movement of the lever.

3. The delivery system according to claim 1, further comprising a reinforcement member for hindering backlash movement of the connection rod, wherein the pawl is adapted to lift the reinforcement member and thereby release the connection rod.

4. The system according to claim 1, further comprising a brush.

5. The system according to claim 1, further comprising a material selected from the group consisting of: enzyme-containing compositions; dental primers; bondings; etching gels; etching liquids; varnishes; glue; pharmaceutical liquids; pharmaceutical gels; a substance for the treatment or prevention or identification of caries; a substance for the prevention or identification or removal of plaque; a substance for root canal treatment; a substance for the removal of carious or decayed or infected dentine or enamel; and a substance for the removal of denatured dentine.

6. Kit comprising the system according to claim 5, further comprising a component selected from the group consisting of a dental instrument; a disposable cartridge; a glove; and a bonding or etching agent.

7. A delivery system for controlled dispensing of a substance, the system comprising:
   a cartridge having at least two compartments for storing material components, each of the at least two compartments having an outlet at a front end, wherein the system is adapted to mix the components to form a substance;
   a plunger having at least two pistons for sealing the respective compartments and advancing material components in the at least two compartments;
   a mixing means for receiving the material components from the at least two compartments and for mixing the material components;
   a sleeve which is movable over the exterior surface of the cartridge;
   a reservoir for receiving the mixed substance from the mixing means, wherein the reservoir is formed by an interior surface of the sleeve and an exterior surface of the cartridge, wherein a cavity is formed within the reservoir;
   a lever and a geared connection rod for providing controlled dispensing of the substance; and
   a self-opening closure system which seals the front ends of the at least two compartments and opens when the plunger is advanced;
   wherein the lever is attached to the sleeve, and a pawl engages with the lever so that upon each push of the lever, the cartridge is caused to move forward toward the cavity thereby providing controlled dispensation of the substance.

* * * * *